United States Patent [19]

Cheiman

[11] Patent Number: 5,908,158
[45] Date of Patent: Jun. 1, 1999

[54] ULTRASONIC NEBULISING DEVICE

[75] Inventor: Vladimir Cheiman, Bondi Junction, Australia

[73] Assignee: Sheiman Ultrasonic Research Foundation Party, Ltd., Australia

[21] Appl. No.: 09/003,740

[22] Filed: Jan. 7, 1998

Related U.S. Application Data

[63] Continuation of application No. 08/416,812, filed as application No. PCT/AU93/00530, Oct. 15, 1993, abandoned.

[30] Foreign Application Priority Data

Oct. 16, 1992 [AU] Australia ............................. PL 5297
Jul. 27, 1993 [AU] Australia ............................. PM 0155

[51] Int. Cl.$^6$ ............................................. B05B 17/06
[52] U.S. Cl. ............................. 239/102.2; 128/200.16; 261/DIG. 78
[58] Field of Search .................. 239/102.1, 102.2, 239/499, 304; 261/DIG. 48, DIG. 78; 128/200.16, 200.18

[56] References Cited

U.S. PATENT DOCUMENTS

| 4,410,139 | 10/1983 | Nishikawa et al. ............... 239/102.2 |
| 4,641,053 | 2/1987 | Takeda .......................... 239/102.2 X |
| 4,708,826 | 11/1987 | Mizoguchi ...................... 239/102.1 X |
| 5,217,165 | 6/1993 | Takahashi et al. ............... 239/102.2 |
| 5,300,260 | 4/1994 | Keshet et al. .................. 239/102.2 X |

FOREIGN PATENT DOCUMENTS

| 119114 | 9/1979 | Japan . |
| 10367 | 2/1981 | Japan . |
| 100247 | 8/1981 | Japan . |
| 168995 | 11/1972 | New Zealand . |

*Primary Examiner*—Lesley D. Morris
*Attorney, Agent, or Firm*—Ostrolenk, Faber, Gerb & Soffen, LLP

[57] ABSTRACT

The device is designed for nebulizing liquids and for transporting the formed aerosols. It includes components to form a fountain of liquid that is being nebulized, a container holder (4), a container (2) with contact medium (3), an additional container (5) with liquid being nebulized (6), a nebulization chamber (7), a system for transporting the aerosol to the user, an outlet duct (11), and a mechanism for regulation of rate of delivery of aerosol. The nebulization chamber (7) is designed as a double-element structure, composed of an intake tube (8) and an expansion chamber (9). In the bottom of the expansion chamber (9) outlets (10) have been made for the drainage of the non-nebulized liquid back to the section of the container remote from the base of the fountain. This reduces the negative action of the non-nebulized liquid on the effectiveness of nebulization. The expansion chamber (9) which is incorporated into the nebulization chamber (7) ensures a significant reduction in coagulation of the aerosol particles, thus increasing the efficiency of the nebulizer and particle uniformity. The latter effect is likewise heightened by this specifically designed outlet duct (10) which accomplishes a process of gravitational filtration. As a consequence of the movement of the stream in the narrow intake tube (8) there is formation of a differential pressure, enabling transport of the aerosol from the nebulization chamber to the user. The above principles are proposed for application to multi-use and single-used devices.

11 Claims, 5 Drawing Sheets

F I G. 2A
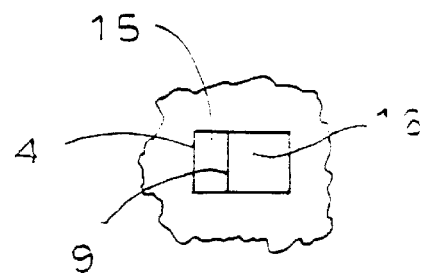
F I G. 4A
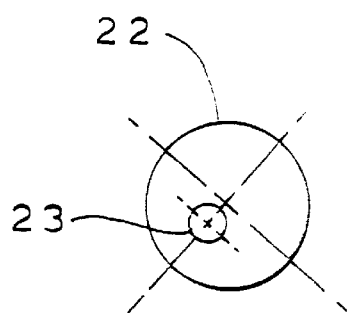
F I G. 9
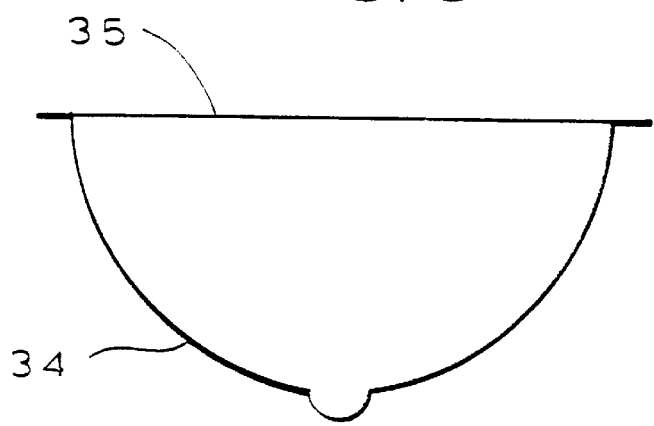

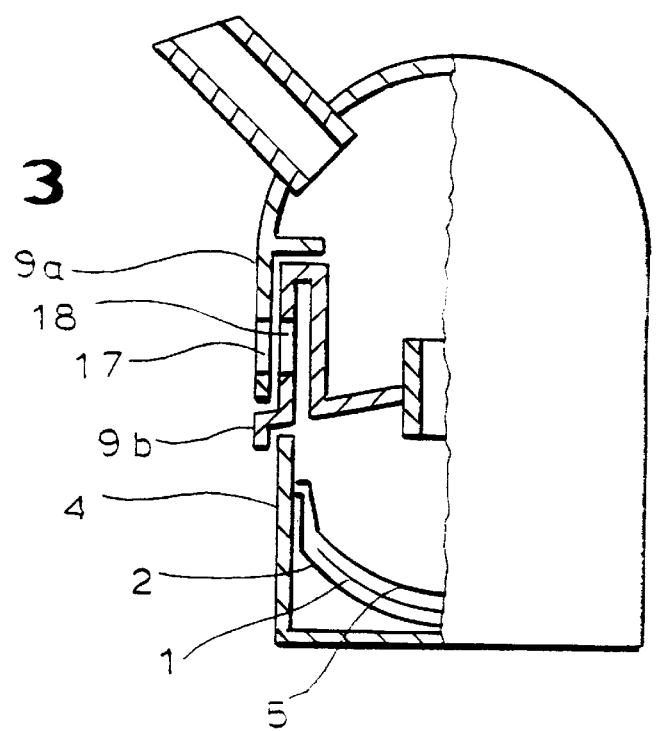
F I G. 3
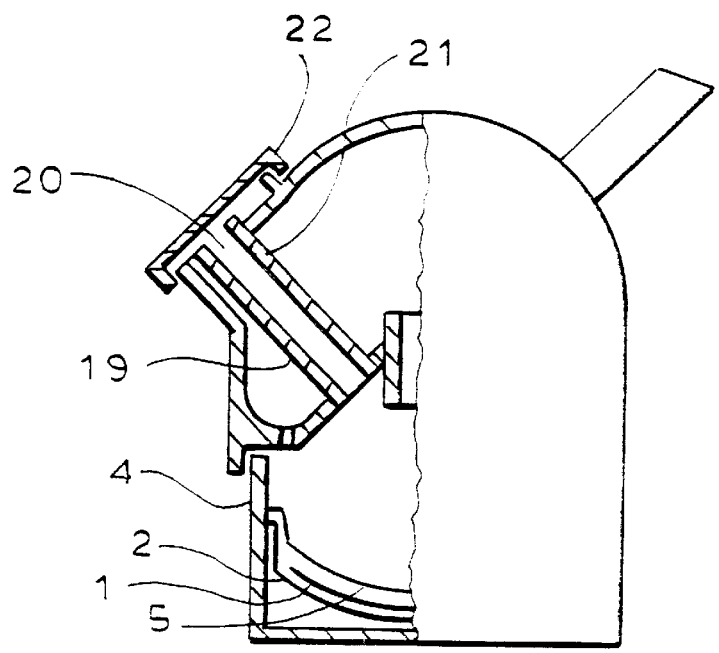
F I G. 4

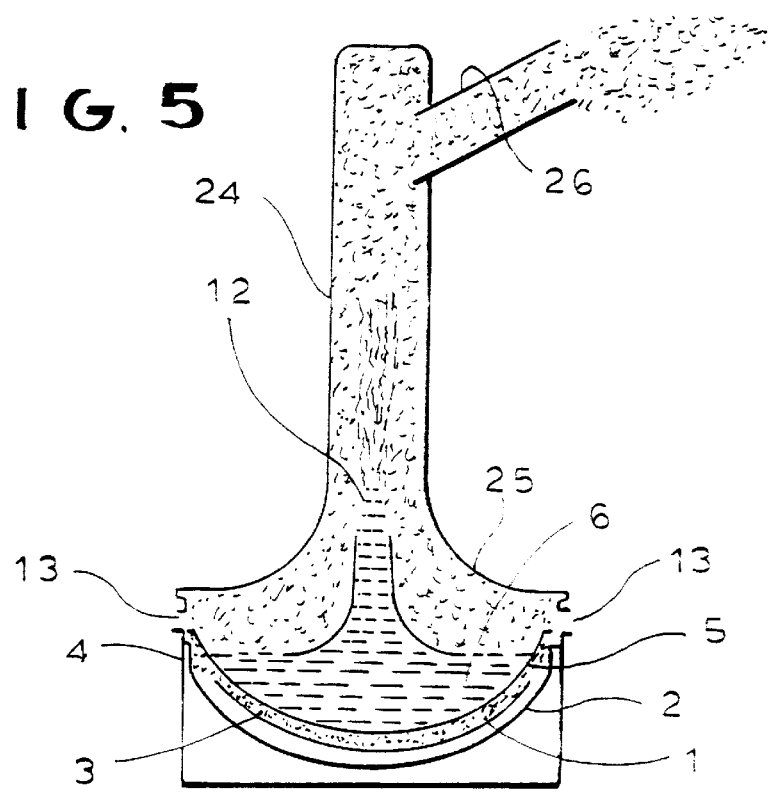
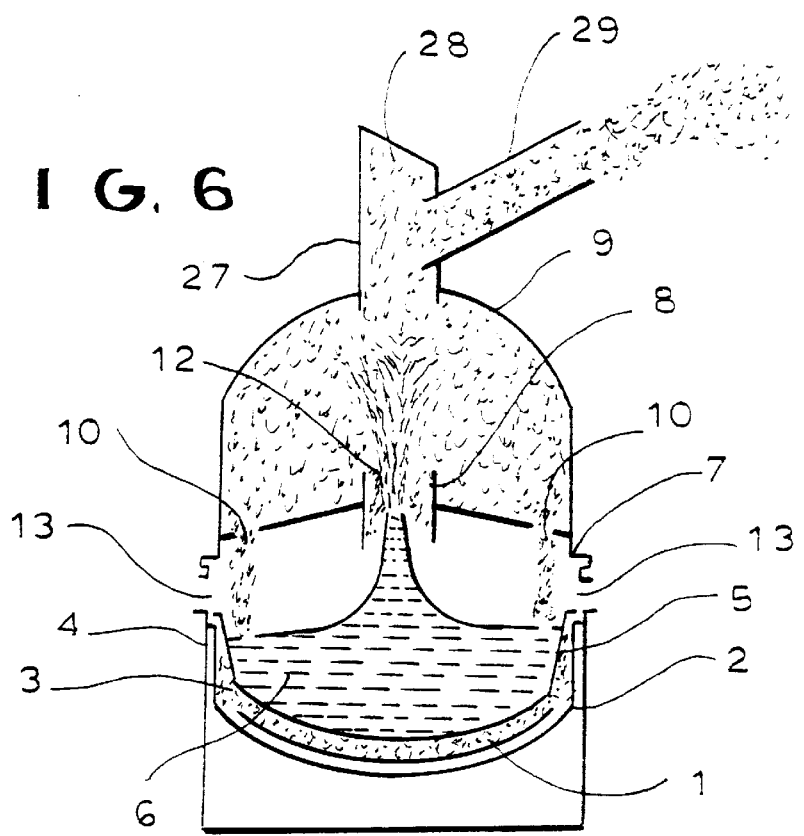

ULTRASONIC NEBULISING DEVICE

This application is a continuation of application Ser. No. 08/416,812 filed Apr. 13, 1995, abandoned, which was a national stage of PCT/AU93/00530 filed Oct. 15, 1993.

FIELD OF THE INVENTION

This invention relates to the device for nebulizing liquid and for transporting the formed aerosols.

BACKGROUND OF THE INVENTION

Ultrasonic nebulizers are widely used for the inhalation of medications, nebulization of liquid fuel, moisturisation of air and for other uses.

A typical device for the nebulization and transport of aerosol which is used in ultrasonic nebulizers is described on p.298 of "Utrasound" (in Russian) in the series "Small Encyclopedia", published by "Soviet Encyclopedia" Publishing House, Moscow 1979.

The disadvantage of this device is the return of a large proportion of non-nebulized liquid reflected from the fountain shield back to the liquid being nebulized in the area of the active part of the fountain (i.e. the base), where the intensity of the ultrasound is maximized. This results in both a higher load on the ultrasonic transducer as well as increased waviness of the liquid being nebulized, thus defocusing transmitted energy. Both of these factors reduce effectiveness and stability of nebulization.

It is known that drops of liquid (and particles of aerosol) returning to the container have a higher temperature than the liquid that is being nebulized because of the work necessary for their creation through which they have absorbed added energy. Where these drops return to the liquid being nebulized, the temperature of the liquid changes according to random law. This further destabilises the acoustic characteristics of the medium, intensifying defocusing and lowering efficiency and stability of nebulization.

The other disadvantage of this device is the need of a separate fan for transporting the aerosol to the user.

Some of the disadvantages in the above-mentioned device are avoided in U.S. Pat. No. 4,410,139 issued Oct. 18, 1984. As shown in this patent to reduce the influence which the returning non-nebulized liquid has on effectiveness and stability of the nebulization, the ultrasonic transducer is placed at an angle different from ninety degrees to the axis of the nebulization chamber. On the bottom of the container of this device a slotted partition which surrounds the fountain is set up. It is positioned so that the major portion of the non-nebulized liquid falls outside the perimeter of the partition.

This device has some disadvantages, which reduce its efficiency and complicate its construction. The main disadvantages are:

1. The necessity to put an ultrasonic transducer at an angle to the surface of the liquid being nebulized, which leads to the significant complications in the construction of its mounting in the container holding the liquid being nebulized and therefore increases the dimensions of the said container..
2. Asymmetry of the nebulization process caused by the axis of the fountain being positioned at an angle to the axis of the container, thus leading to:
  a) Increase in waviness of the liquid which then increases defocusing of transmitted energy.
  b) Reduction of nebulization efficiency at low levels of liquid, caused by the liquid's surface being non-perpendicular to the direction of propagation of the ultrasonic wave front.
3. Additional losses caused by dissipation on the partition of the energy of the ultrasonic wave which passes through the liquid being nebulized.
4. A need for a fan to effect aerosol transport.

In summary, even though the outlined device allows certain improvement in the efficiency of nebulization, its disadvantages mentioned above restrict substantially its effectiveness.

The object of this invention is the creation of an improved device for nebulization of liquid and transport of aerosol assuring higher efficiency and stability as well as greater uniformity of the aerosol particles and delivery of the aerosol to the user without the need of an added fan; this is to be provided by means of diverting the major portion of the recycled non-nebulized liquid to the area of the container remote from the base of the fountain and the establishment (for transport of the aerosol) of a differential air pressure by reducing the cross-section of a part of the channel along which the stream of the fountain moves (Bernoulli's Law).

This object is achieved by means of designing the nebulization chamber in two parts: the expansion chamber including a bottom in which one incorporates outlet(s), as well as an intake tube inserted in the bottom of the expansion chamber and located above the base of the fountain stream of liquid being nebulized; the system of transport of the aerosol to the user is accomplished in the form of the above mentioned intake tube, and inlet(s) located on any section of the nebulizer with/without a supplementary tube(s) connected to the inlet(s) and passing through any section of the nebulizer in order for the outside air to enter by means of free (unforced) flow into the intake tube from the side of the container holding the liquid being nebulized.

BRIEF DESCRIPTION OF THE DRAWING

FIG. 3 is a vertical sectional view of the second modification of the mechanism for regulation of the rate of aerosol delivery.

FIG. 4 is a vertical sectional view of the third modification of the mechanism for regulation of the rate of aerosol delivery.

FIG. 5 is a vertical sectional view of the modification of the nebulizer embodying a single-part construction of nebulization chamber.

FIG. 6 is a vertical sectional view of outlet duct (installed in the nebulizer) for reduction of incidental droplets at the exit point.

FIG. 9 is a vertical sectional view of the hermetically closed additional container.

DETAILED DESCRIPTION

Figure 1:
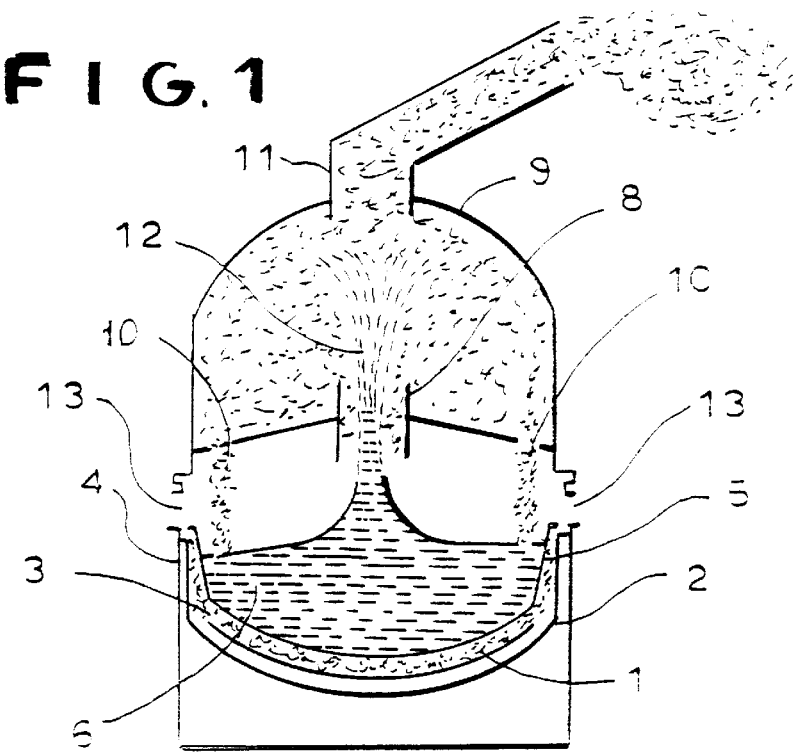
FIG. 1 is a vertical sectional view of the nebulizer embodying the present invention.

The subject is illustrated in FIG. 1.

Ultrasonic transducer (1) is positioned in the container (2), which is filled with contact medium (3) and mounted in the container holder (4). In the container (2) is installed an additional container (5) which is filled with the liquid being nebulized (6). Above the liquid being nebulized the nebulization chamber (7) is positioned, consisting of an intake tube (8) and an expansion chamber (9). In the bottom of the expansion chamber, outlet(s) (10) is/are made. In the expansion chamber an outlet duct (11) is placed. When the device is functioning the liquid forms an ultrasonic fountain (12), which runs via the intake tube into the expansion chamber. The active part of the fountain of liquid that is being nebulized, where the speed of stream is maximum comes through the intake tube. In this instance one reduces the cross-section of the channel for the stream of cavitation liquid of the fountain, combined with the cloud of aerosol. Due to this, according to Bernoulli's Law, a differential air pressure is established, directed from the intake tube to the expansion chamber. This differential pressure is the driving force for transport of the aerosol from the expansion chamber to the user. For the replenishment of the air which transports the aerosol, inlet(s) (13) is/are made, through which outside air by means of free (unforced) flow is passed to the hole of the intake tube which faces the liquid being nebulized. These inlet(s) may be located on any section of the device and are linked with the above mentioned point of entry of the outside air with or without the aid of additional tube(s). The fountain stream upon reaching a certain height begins to disintegrate, resulting in sprinkles, the major portion of which fall mostly past the area of the intake tube and closer to the walls of the expansion chamber. The falling sprinkles return in the form of the drops to the container with liquid being nebulized through the outlets of the expansion chamber, which are situated in such a way that the liquid comes to the section of the container which is remote from the active part of the fountain.

Such construction allows:

1. Reduction of the load on the ultrasonic transducer, caused by the falling of the drops of non-nebulized liquid from the nebulization chamber to the container with liquid being nebulized. This is attained by the specific placing of the outlets in the bottom of the nebulization chamber in connection with which most of the drops fall in the area of the container away from the base of the fountain (where the main part of ultrasonic energy is focused). In this area the intensity of ultrasound is low, therefore the acoustic loss which is caused by the falling of drops into the container will be insignificant.
2. Lowering of the speed of the said falling drops (mentioned in item 1), on account of the sprinkles having to overcome the forces of attachment and friction during the movement along the wall of the expansion chamber and the forces of attachment and surface tension during drainage through the outlets.

The lowering of the speed increases the time for the temperature of the drops to approach the surrounding temperature and lowers the kinetic energy of the drops at the time that they fall into the liquid being nebulized. Both of these factors weaken the waviness on the surface of the liquid being nebulized which is caused by the falling of the drops and because of this weaken the defocusing of the ultrasonic energy in the area of the base of the fountain. The lowering of defocusing is likewise promoted by the fact that the majority of the drops fall at a distance from the base of the fountain.
3. Lowering of the coagulation of aerosol particles, because its path through the narrow intake tube to the user goes through the expansion chamber where the space accessible to the aerosol is enlarged, thus significantly reducing the likelihood of coagulation and increasing of the uniformity of the particles.
4. Lowering the amount of functioning components by eliminating the need of a fan to drive the nebulized aerosol.

The outline in items 1–4 conclusively shows that the proposed construction increases the efficiency and stability of nebulization (items 1,2,3), uniformity of aerosol (items 2,3), functional reliability (item 4); eliminates operational noise (item 4); simplifies the system of transport of aerosol (item 4); reduces power consumption, as well as dimension and cost of the device (items 1,2,3,4).

To reduce the aggregation of the non-nebulized part of the liquid in the expansion chamber, the bottom of the nebulization chamber should be placed at an angle to the intake tube, different from 90 deg. (FIG. 1).

The regulation of quantity of aerosol which is released from this device can be accomplished by changing the volume of air flowing to the hole in the intake tube which faces the liquid being nebulized. This is achieved by means of alteration of a cross-section of any part of the air channel, linking the inlet(s) with the above mentioned point of entry of the air.

Figure 2:
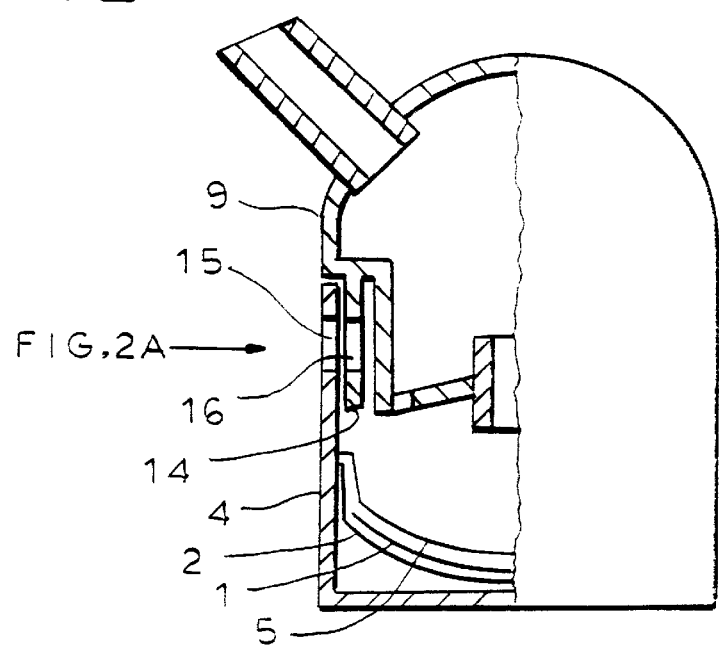
FIG. 2 is a vertical sectional view of the first modification of the mechanism for regulation of rate of aerosol delivery.

The design of one of the regulation mechanism modifications is shown in FIG. 2. In this instance the expansion chamber has added to it the component (14) of the regulator which is rigidly linked to the chamber. The lateral surface of the regulation component is parallel to the lateral surface of the container holder (4). Hole (15) is made on the lateral surface of the regulation component and hole (16) on the lateral surface of the container holder. The volume of air flowing to the intake tube through these holes is regulated by rotation of the expansion chamber (9) in relation to the container holder (4). In this as well as the subsequent designs for regulation the maximum volume of air ( and therefore maximum intensity of aerosol at the outlet duct) will be obtained for the exact superimpositions of holes (15) and (16), whilst the minimum volume of air (and therefore minimum intensity of aerosol at the outlet duct)—for complete closure of the holes.

For a nebulization chamber design consisting of two parts (9a) and (9b) (FIG. 3), both parts or one of them, by analogy with FIG. 2 have added on a regulator component incorporating a hole and which is rigidly linked to the chamber. Again, the lateral surface of the regulator component is parallel to the lateral surface of that part of the nebulizer where the hole is covered over during the regulation process. The mode of regulation by means of rotation of the hole (17) in the upper part (9a) of the expansion chamber in relation to the hole (18) in the lower part (9b) of the expansion chamber is shown in FIG. 3.

It is also possible to deliver air to the intake tube through holes (19) and (20) in the nebulization chamber connecting with each other by tube (21) (FIG. 4). In this instance for regulation one introduces a lid (22), with hole (23), which is positioned eccentrically to the tube (21) in which is located hole (20). Rotation of the lid with the hole around the tube will alter the cross-section of the resultant hole between the lid and the tube.

In the case when reduction of the device is important, the two-part design of the nebulization chamber can be converted into a single-part design. In such a design the nebulization chamber appears as an extended intake tube (24) (FIG. 5). The lower part (25) of the intake tube is expanded in order to redirect that part of the non-nebulized liquid which runs down its sides to the area of the container remote from the base of the fountain. Here the expanded part of the intake tube fulfills similar functions to the outlets in the bottom of the expansion chamber of the device shown in FIG. 1.

In order to reduce incidental droplets reaching the user through the outlet duct (26), the latter is made in the shape of a tube which is attached to the nebulization chamber below its summit. The summit of the nebulization chamber plays the role of a reflector for the droplets.

In the nebulizer where the droplets may reach the user, optimal design of the outlet duct should consist of two tubes joined at an angle (FIG. 6). The tube (27) which emerges from the expansion chamber must have a reflector (28) at its summit, located at an awe to the axis of the fountain. The tube (29) which goes to the user joins the above-named tube at a point below the reflector. Such an outlet duct allows the reduction of incidental droplets at the exit point.

Figure 7:
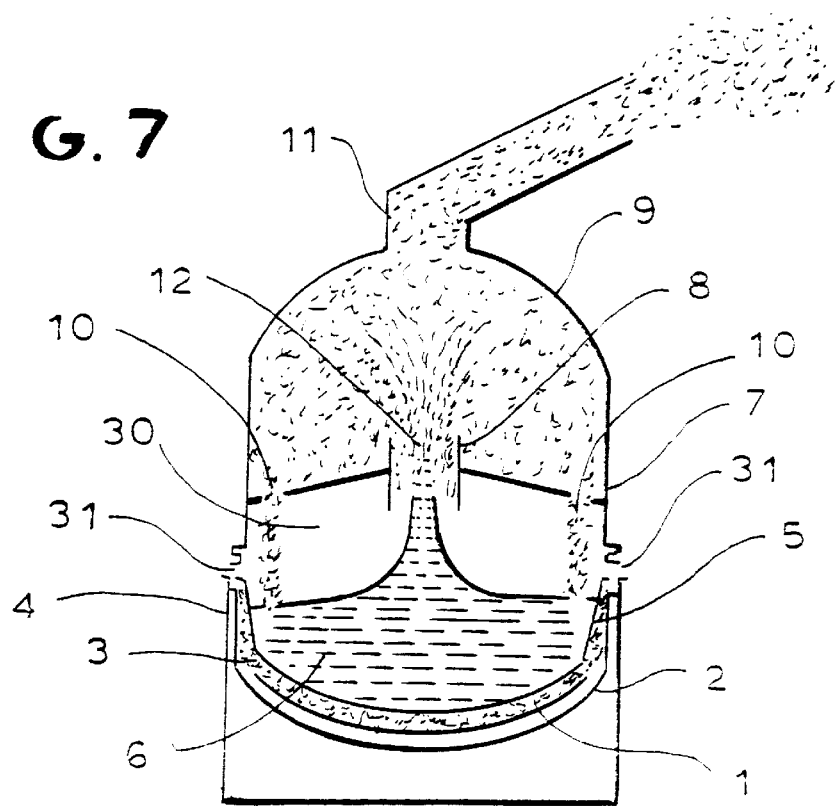
FIG. 7 is a vertical sectional view of the closed nebulization system.

To facilitate the sterilization of the nebulizer, from the components of the device in FIG. 1 or in FIG. 5 is designed a removable single-use unit, which is linked to the ultrasonic transducer through a contact medium and which combines within itself the functions of storage and nebulization of the liquid, as well as transport of the aerosol. This unit is constructed (FIG. 7) by joining the lower part of the nebulization chamber (7) to the upper part of the additional container (5) both the chamber and additional container being designed according to FIG. 1. In this context the surface of the lower part of the nebulization chamber forms in conjunction with the surface of the additional container another chamber (30). On the surface of this chamber is/are inserted inlet(s) (31) through which outside air may reach the intake tube by means of free (unforced) flow from the side of the liquid being nebulized. These/this inlet(s) may be located on any section of the device and are linked with the above mentioned point of entry of the outside air with or without the aid of additional tube(s) by analogy with the designs in FIGS. 1–4 incl.

The device as described realizes under the action of the ultrasound energy the full cycle of formation of aerosol and its transport to the user, i.e., represents a closed nebulization system. Its operation is identical with that of the device shown in FIG. 1.

Figure 8:
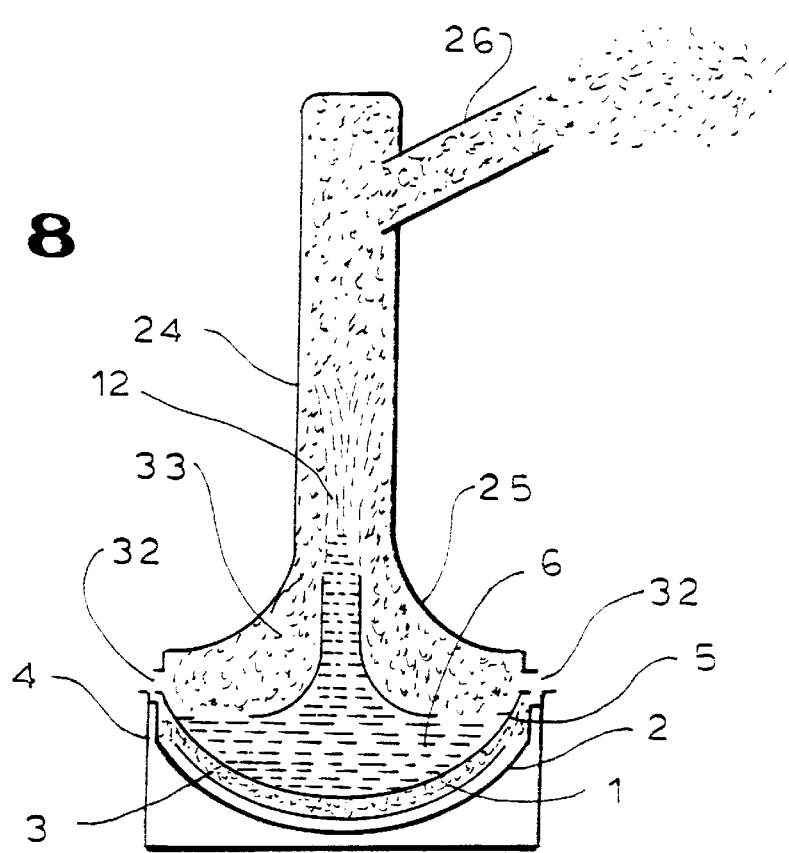
FIG. 8 is a vertical sectional view of the modification of the closed nebulization system.

The other modification of the closed nebulization system follows from the design of the nebulization device in FIG. 5 and is shown in FIG. 8. This modification reproduces entirely the design principles outlined above, with the only difference in this case being that the nebulization chamber (24) is constructed as shown in FIG. 5, rather than FIG. 1 in the case of the previous example. At the same time inlet(s) (32) are incorporated on the surface of the chamber (33) created by joining the lower part (25) of the nebulization chamber (24) to the upper part of the additional container (5) similar to the inlet(s) (31) of the chamber (30) in FIG. 7. The operation of this modification of the closed nebulization system corresponds entirely to that of the nebulizer shown in FIG. 5.

In those cases, when the requirement for the sterility applies only to the contents of additional container, this container is constructed as a hermetically closed vessel (34) (FIG. 9) which may be opened by action of ultrasound or other forms of energy. As one modification the lid (35) of the additional container may be made of elastic material, which, with the exertion of energy at its center, is ruptured and contracts to its periphery, thus allowing access of the liquid being nebulized to the nebulization chamber.

I claim:

1. A nebulizer having a holding chamber adapted to hold liquid to be nebulized, an ultrasonic transducer positioned below the holding chamber and arranged upon activation to cause a fountain of liquid to spout upwardly within the holding chambers an air inlet allowing air to flow to the vicinity of the fountain for nebulization of the liquid as aerosol, and an outlet duct for discharge of the aerosol, the nebulizer comprising a tube positioned in the upper part of the holding chamber such that liquid from the fountain spouts into the lower end of the tube where the aerosol is produced, the tube having a restricted cross-sectional area relative to the chamber such that the kinetic energy of the fountain increases the static pressure of the aerosol within the tube thereby inducing a pressure drop between the tube and the outlet duct which alone is sufficient to propel the aerosol nebulized from the fountain upwardly through the tube to the outlet duct under the assistance of air being drawn into the holding chamber via the air inlet.

2. A nebulizer as claimed in claim 1 wherein the tube opens at its upper end into an expansion chamber in turn communicating with the outlet duct.

3. A nebulizer as claimed in claim 2 wherein the expansion chamber is adapted to contain any un-nebulized drops of liquid issuing from the tube and drain the liquid back into the holding chamber at a location remote from the fountain.

4. A nebulizer as claimed in claim 3 wherein the expansion chamber has a floor extending outwardly and downwardly from the tube and one or more apertures in the floor toward the outside of the expansion chamber adapted to drain liquid into the holding chamber.

5. A nebulizer as claimed in claim 4 wherein the upper part of the expansion chamber is domed allowing un-nebulized liquid to collect on the inside walls of the expansion chamber and drain down those walls to the lower part of the expansion chamber.

6. A nebulizer as claimed in claim 1 wherein the outlet duct opens from one side of the tube adjacent the upper end of the tube which is closed causing any un-nebulized drops of liquid to gather on the walls of the tube or impinge upon the closed upper end of the tube and drain down the walls of the tube into the holding chamber.

7. A nebulizer as claimed in claim 1 wherein the lower end of the tube flares outwardly into the upper part of the holding chamber, causing liquid draining down the walls of the tube to adhere to the outwardly flaring wall before dropping into the liquid in the holding chamber at a location remote from the fountain.

8. A nebulizer as claimed in claim 1 wherein the air inlet is controllable by the user to vary the rate at which the liquid is nebulized.

9. A nebulizer as claimed in claim 8 wherein the air inlet is controllable by relative movement of two components each having an aperture therethrough, said movement bringing the apertures into and out of register.

10. A nebulizer as claimed in claim 1 wherein the liquid to be nebulized is contained within an hermetically closed vessel adapted to be inserted into the holding chamber, the upper part of the vessel being closed by a membrane adapted to be ruptured and opened before use.

11. A nebulizer as claimed in claim 1 wherein at least the holding chamber and the tube are provided as a sealed unit containing the liquid to be nebulized, and wherein the sealed unit is engageable with the remainder of the nebulizer before use and is adapted to be discarded after use.

* * * * *